United States Patent
Weng (10) Patent No.: US 8,863,593 B2
(45) Date of Patent: Oct. 21, 2014

(54) SAMPLING DEVICE AND METHOD (75) Inventor: Yanwen Weng, Shenzhen (CN)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 614 days.

(21) Appl. No.: 13/149,427

(22) Filed: May 31, 2011

(65) Prior Publication Data

US 2012/0000296 A1 Jan. 5, 2012

(30) Foreign Application Priority Data

Jul. 5, 2010 (CN) .......................... 2010 1 0216544

(51) Int. Cl.
*G01N 1/14* (2006.01)
*G01F 25/00* (2006.01)
*G01N 35/10* (2006.01)

(52) U.S. Cl.
CPC .............. *G01N 35/1011* (2013.01); *G01N 1/14* (2013.01); *G01N 2035/1025* (2013.01); *G01F 25/0092* (2013.01)
USPC .................. 73/863.01; 73/863.02; 73/864.24; 73/864.73

(58) Field of Classification Search
CPC .. G01F 25/0092; G01N 1/14; G01N 35/1011; G01N 2035/1025
USPC .............. 73/863.01–863.03, 864.24–864.25, 73/864.73
See application file for complete search history.

(56) References Cited

U.S. PATENT DOCUMENTS 3,474,902 A * 10/1969 Putman .......... G01N 2035/1025
3,853,010 A * 12/1974 Christen et al. ............ 73/864.24
4,410,020 A    10/1983 Lorenz
4,905,526 A *  3/1990 Magnussen et al. ..... G01N 1/14
5,098,660 A *  3/1992 Devaney, Jr. ................ 422/82.12
5,139,744 A *  8/1992 Kowalski ........................ 422/67
5,314,825 A *  5/1994 Weyrauch et al. . G01N 35/1011
6,787,111 B2 * 9/2004 Roach et al. ................... 422/509
7,186,378 B2 * 3/2007 Dunfee .............. G01N 35/1011
7,603,899 B2 * 10/2009 Li et al. ........... G01N 2035/1025
7,647,847 B2 * 1/2010 Kitagawa et al. .......... 73/864.86
8,470,241 B2 * 6/2013 Rivas et al. ............. G01N 35/10
8,778,686 B2 * 7/2014 Kuroda .................. G01N 35/10
2009/0044607 A1   2/2009 Hochgraeber et al.
2010/0132487 A1 * 6/2010 Haack et al. ....... G01N 35/1011
2012/0291872 A1 * 11/2012 Brady et al. ...................... 137/3
2014/0152326 A1 * 6/2014 Zuppiger ........... G01N 35/1011

FOREIGN PATENT DOCUMENTS

CN    2334031 Y    8/1999
CN    1928526 A    3/2007
CN    101135584 A   3/2008
CN    101655423 A   2/2010

(Continued)

*Primary Examiner* — Thomas P Noland (74) *Attorney, Agent, or Firm* — Kory D. Christensen; Stoel Rives LLP (57) ABSTRACT

Disclosed is a sampling device and method for detecting liquid. The device includes a sampling probe; an action module for actuating the sampling probe; a control module for controlling the action module; a detection module for detecting a change of a relevant physical quantity of the sampling probe and converting the physical quantity into a corresponding electric signal output to the control module. The control module processes the electric signal output by the detection module and controls the action module to actuate the sampling probe based on the electric signal. The device is capable of determining abnormal liquid suction situations, making the sampling more reliable.

15 Claims, 5 Drawing Sheets

(56) References Cited

FOREIGN PATENT DOCUMENTS

| EP | 253685 | A | * | 1/1988 | ............. | G01N 35/10 |
| EP | 0865824 | A1 | * | 9/1988 | ............. | G01N 35/10 |
| EP | 1226867 | A2 | * | 7/2002 | ............... | B01J 19/00 |
| WO | WO 8706008 | A2 | * | 10/1987 | ............. | G01N 35/00 |
| WO | WO 9716714 | A1 | * | 5/1997 | ............... | G01N 1/00 |
| WO | WO 0137996 | A1 | * | 5/2001 | ............. | G01N 35/10 |
| WO | WO 02079751 | A2 | * | 10/2002 | ..... | G01N 2035/1025 |

\* cited by examiner

SAMPLING DEVICE AND METHOD

CROSS-REFERENCE TO RELATED APPLICATION(S)

This application claims the benefit of Chinese Patent Application No. 201010216544.3, filed on Jul. 5, 2010, which is incorporated herein by reference in its entirety.

TECHNICAL FIELD

The present disclosure relates to sampling devices and, more particularly, to medical sampling devices.

SUMMARY OF THE INVENTION

Disclosed herein are sampling devices and methods that detect abnormal liquid suction situations.

DETAILED DESCRIPTION

In a sampling system, a sampling probe must provide sufficient suction for a target liquid. Typically, open-loop control systems are used. The sampling probe stops moving after a liquid surface detection system detects that the sampling probe contacts a target liquid surface, and then performs subsequent actions, such as liquid suction.

In actual operation, however, interferences usually exist. Sometimes, before the sampling probe truly contacts the target liquid surface, the liquid surface detection system mistakenly determines that the sampling probe contacts the real liquid surface. This has a great impact on subsequent operations.

For example, when a bubble exists on a liquid surface to be tested, the sampling probe contacts the bubble, and the bubble exerts certain impact on the liquid surface detection system, to cause the system to mistakenly determine that the liquid surface is detected. Consequently, the sampling probe stops moving and performs subsequent actions like liquid suction, resulting in an incorrect test result. Besides a bubble, other interference factors, such as static electricity and electromagnetic interference, may also cause the liquid surface detection system to incorrectly determine that the liquid surface has been touched before the sampling probe contacts the real liquid surface.

Furthermore, the sampling probe may depart from the liquid surface when sucking the liquid, resulting in insufficient liquid suction. In this case, the subsequent actions may result in an incorrect test result if the amount of the target liquid is insufficient.

Various attempts have been made to solve the problem of insufficient liquid suction. First, a stop position of the sampling probe may be determined, in which the previous stop position of the sampling probe is recorded first. The current stop position is compared with the previous stop position, and the exceeding part of the position differential is regarded as being affected by interference. This method has the defect of being only applicable in a closed system, and is incapable of determining the situation of insufficient liquid suction.

Second, a pressure sensor may be added, i.e., pressure data in liquid suction is analyzed to detect whether asuction-without-liquid phenomenon appears. This method requires a set of pressure detection systems, resulting in high cost. Meanwhile, the detection can only be performed in the liquid suction process, and fails to work under a situation that the liquid suction amount is slightly lower than the target value.

Third, a certain height limit is set to ensure sufficient liquid suction. This method may cause a great amount of remaining liquid and raise requirements for relevant mechanical designs.

Accordingly, the present disclosure is directed to a sampling device and method capable of determining abnormal liquid suction situations. In one aspect, the sampling device includes a sampling probe; an action module for actuating the sampling probe; a control module for controlling the action module; a detection module for detecting a change of a relevant physical quantity of the sampling probe and converting the physical quantity into a corresponding electric signal output to the control module, wherein the control module processes the electric signal output by the detection module, and controls the action module to actuate the sampling probe based on the electric signal.

In one embodiment, when the sampling probe fails to contact the real liquid surface or confronts interferences, e.g., the sampling probe only contacts a bubble on the liquid surface, a relevant physical quantity of the sampling probe, such as an equivalent capacitance value, an equivalent resistance value, or other physical quantities of the sampling probe, changes. Therefore, the changed physical quantity can be detected using the detection module of the corresponding sensor to complete a preliminary determination of whether the sampling probe contacts the liquid surface. Compared with the real liquid surface, the suddenly changed relevant physical quantity of the sampling probe caused by the interference is difficult to maintain. On the other hand, if the sampling probe contacts the real liquid surface, the relevant physical quantity of the sampling probe also suddenly changes but remains stable.

For example, the most common interference includes a bubble on the liquid surface. Due to its fragile characteristics, a bubble is typically punctured when contacting the sampling probe, so it remains in existence for a short time. When the sampling probe contacts the bubble, the relevant physical quantity of the sampling probe changes, and when the bubble bursts, the relevant physical quantity of the sampling probe recovers to a value approximate to the value before contacting the bubble. Therefore, by detecting the relevant physical quantity of the sampling probe and analyzing and processing accordingly, it can be found whether the sampling probe contacts the real liquid surface during sampling.

The sampling probe gradually approaches the surface of the liquid to be sampled, stops moving when contacting the liquid surface, and starts sampling. Then, in the liquid suction process, if the sampling probe departs from the liquid surface, insufficient liquid suction is caused, and the relevant physical quantity of the sampling probe also changes. Whether the liquid sucked by the sampling probe is insufficient can be determined by detecting the change.

In one embodiment, the sampling probe is made of a conducting material. The relevant physical quantity of the sampling probe detected by the detection module may be an equivalent capacitance value. The detection module may include a phase-lock loop, an amplification circuit, and an analog-to-digital (A/D) conversion circuit.

The phase-lock loop is used for detecting the equivalent capacitance value of the sampling probe, and converting the equivalent capacitance value into a corresponding analog voltage signal. The amplification circuit is used for amplifying the analog voltage signal output by the phase-lock loop. The A/D conversion circuit is used for converting the analog voltage signal output by the amplification circuit into a corresponding digital signal, and outputting the digital signal to the control module. The phase-lock loop may include a phase detector, a loop filter, and a voltage controlled oscillator arranged in a sequentially closed-loop coupled manner. The loop filter outputs the analog voltage signal to the amplification circuit, the voltage controlled oscillator is coupled to the sampling probe, and the phase detector inputs a reference frequency.

In another embodiment, the relevant physical quantity of the sampling probe detected by the detection module is a resistance value. The sampling probe may include a first tube and a second tube separated from each other. The detection module may include an amplification and A/D converting unit for amplifying an input analog electric signal and converting the analog electric signal into a corresponding digital signal, and a current-limiting resistor. The first tube may be coupled to a high voltage level, two ends of the current-limiting resistor are respectively coupled to an input end of the amplification and A/D converting unit and ground, and the input end of the amplifier and A/D converter is further coupled to the second tube and outputs a digital electric signal to the control module.

In yet another embodiment, the relevant physical quantity of the sampling probe detected by the detection module is a resistance value. A container for containing a target liquid may be a conductor and may be grounded. The detection module may include an amplifier and A/D converter for amplifying an input analog electric signal and converting the analog electric signal into a corresponding digital signal, and a current-limiting resistor. One end of the current-limiting resistor may be coupled to an input end of the amplifier and A/D converter and the sampling probe, and the other end may be coupled to a high voltage level.

In still another embodiment, the action module includes a driving unit, a stepper motor, and a rocker arm. The driving unit drives the stepper motor to rotate under the control of the control module. The stepper motor propels the rocker arm to act, and the rocker arm propels the sampling probe to act.

In another aspect, the present disclosure further provides a sampling method, which may include the following steps. While moving a sampling probe toward a sample surface, determining a position of the sampling probe with respect to the sample surface by detecting a change in a physical quantity of the sampling probe; actuating the sampling probe based on the determined position; and in response to determining that the sampling probe contacts the sample surface, performing a sampling operation.

According to another aspect, the present disclosure further provides a sampling method, which includes the following steps. A sampling step may be performed, in which a sampling probe draws a liquid. Additionally, a liquid amount determination step may be performed, in which a relevant physical quantity of the sampling probe is measured and, based on the measured physical quantity, it is determined whether the sampling probe has drawn sufficient liquid.

In one embodiment, the relevant physical quantity of the sampling probe is at least one selected from a group consisting of an equivalent capacitance value, an equivalent resistance value, and an equivalent inductance value of the sampling probe. The preparatory sampling step and the liquid amount determination step may be applied independently or applied together; and if the two steps are both performed, the preparatory sampling step is performed before the liquid amount determination step.

Figure 1:
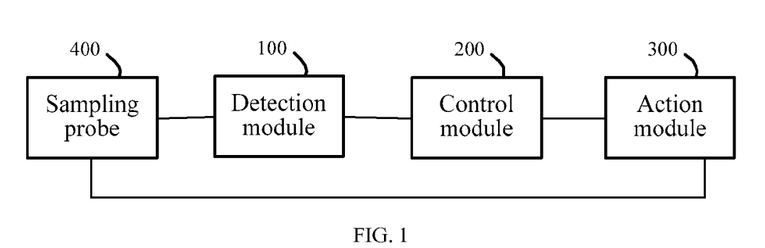
FIGS. 1 and 2 are schematic structural views of a sampling device.

Referring to FIG. 1, a sampling device is shown, which includes a sampling probe 400; an action module 300 for driving the sampling probe 400; a control module 200 for controlling the action module 300, a detection module 100 for detecting a change of a relevant physical quantity of the sampling probe 400, and converting the physical quantity into a corresponding electric signal to the control module 200.

The control module 200 processes the electric signal output by the detection module 100, and controls the action module 300 to actuate the sampling probe 400 accordingly.

Figure 2:
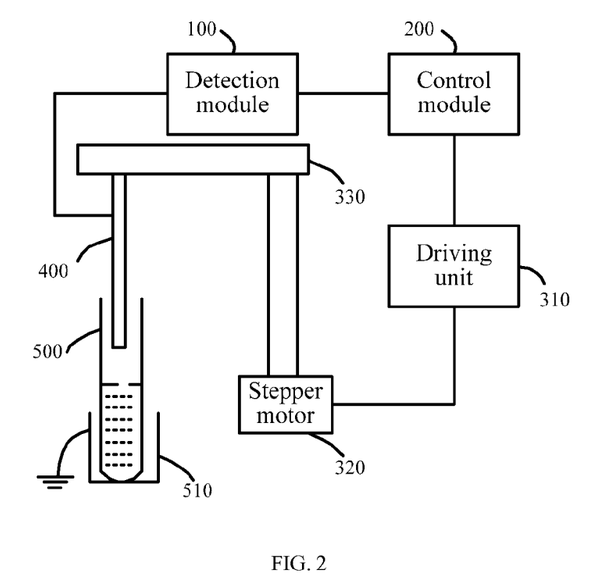

Referring to FIG. 2, the sampling probe 400 may be installed on a rocker arm 330, and the rocker arm 330 may be driven by a stepper motor 320. The control module 200 sends an instruction to a driving unit 310, so that the driving unit 310 drives the stepper motor 320 to move or stop. The detection module 100 is connected to the sampling probe 400, and detects a relevant equivalent physical quantity of the sampling probe and converts the physical quantity into a corresponding digital signal. The control module 200 sends a data transmission instruction to the detection module 100, and the detection module 100 transmits the corresponding digital signal to the control module 200. The control module 200 determines the signal, analyzes whether a liquid surface is touched, or an interference signal exists, or a problem of insufficient sampling occurs, and then guides the subsequent operations.

In order to eliminate interference, a target liquid is contained in a container 500, and the container 500 is disposed in a grounded chassis 510. In one embodiment, the control module 200 may be implemented with a programmable device, such as a micro-controller unit (MCU) or a field programmable gate array (FPGA). The action module 300 may be implemented with an appropriate driving circuit selected according to actual requirements, and the details will not be repeated herein.

Figure 3:
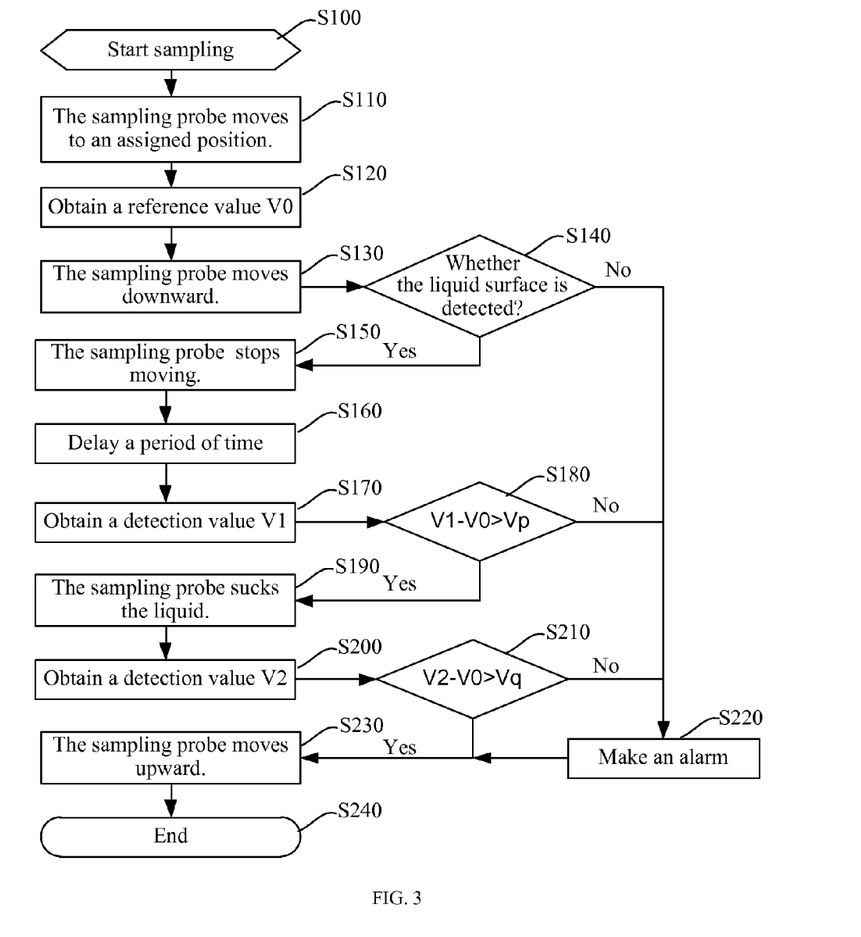
FIG. 3 is a flow chart of a sampling method.
Figure 4:
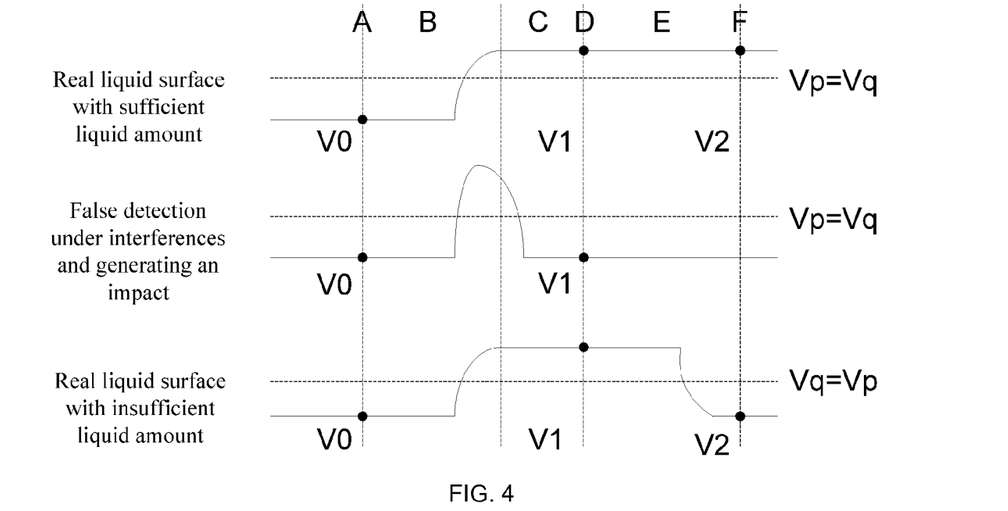
FIG. 4 is a schematic view illustrating changes of a relevant physical quantity of a sampling probe under different conditions in the embodiment shown in FIG. 3.

FIGS. 3 and 4 show a sampling method according to an embodiment of the present disclosure. FIG. 4 reflects changes of the signal output by the detection unit 100 when it is mistakenly determined that the sampling probe contacts the liquid surface, when confronting the interferences, when the sampling probe contacts the real liquid surface and draws sufficient liquid, and when the sampling probe sucks insufficient liquid.

The method may be implemented as shown in FIG. 4.

In Step S100, sampling is started, i.e., sampling of a target liquid s started.

In Step S110, the sampling probe moves to an assigned position, i.e., a position close to and above the target liquid surface.

In Step S120, the detection module obtains a relevant physical quantity of the sampling probe and converts the physical quantity into a corresponding electric signal V0. This process is corresponding to a detection moment A in FIG. 4.

In Step S130, the sampling probe moves downward to reach the target liquid surface.

In Step S140, if the detection module fails to detect a sudden change of the relevant physical quantity of the sampling probe within a certain period of time, Step S220 is performed to make an alarm; while if the detection module detects a sudden change of the relevant physical quantity of the sampling probe within a certain period of time, it is preliminarily determined that the sampling probe contacts the liquid surface. The changes of the signal corresponding to the process are shown in Section B of FIG. 4.

In Step S150, the sampling probe stops moving.

In Step S160, a time delay period commences, and the length of the time delay is determined based on requirements of a time sequence. The time delay is generally less than 1 s., and corresponds to Section C in FIG. 4.

In Step S170, the detection module obtains the relevant physical quantity of the sampling probe, and converts the physical quantity into a corresponding electric signal V1. This process corresponds to a detection moment D in FIG. 4.

In Step S180, it is determined whether a difference between V1 and V0 exceeds a preset threshold Vp, i.e., it is determined whether a sufficient change still exists between the current relevant physical quantity of the sampling probe and the initial physical quantity before it is preliminarily determined that the sampling probe contacts the liquid surface. If not, Step S220 is performed to make an alarm; otherwise, Step S190 is performed.

In Step S190, the sampling probe draws the liquid. This process corresponds to Section E in FIG. 4.

In Step S200, after the sampling probe completes the liquid suction, the detection module obtains the relevant physical quantity of the sampling probe, and converts the physical quantity into a corresponding electric signal V2. This process corresponds to a detection moment F in FIG. 4.

In Step S210, it is determined whether a difference between V2 and V0 exceeds a preset threshold Vq, i.e., it is determined whether a sufficient change still exists between the current relevant physical quantity of the sampling probe and the initial physical quantity before it is preliminarily determined that the sampling probe contacts the liquid surface. If not, Step S220 is performed to make an alarm; otherwise, Step S230 is performed.

In Step S230, the sampling probe moves upward.

In Step 240, the process ends.

Step S180 is further described with reference to FIG. 4. If the sampling probe contacts the real liquid surface, as the sampling probe is immersed in the liquid surface, a signal apparently different from the signal before the sampling probe contacts the liquid surface is generated, and $V1-V0>Vp$ is satisfied, which indicates that the liquid surface is reliable, and the subsequent operations can be performed. If a signal is generated due to interferences, such as bubble, static electricity, or electromagnetic interference, the bubble may be punctured by the sampling probe, and the time for the static electricity or electromagnetic interference is rather short, so that the sampling probe remains basically the same state before contacting the liquid surface, and $V1-V0>Vp$ is not satisfied. In this case, a problem occurs, and an alarm is made in time to stop the current sampling process. Vp is determined according to a signal difference after the sampling probe is immersed in the liquid surface and before the sampling probe contacts the liquid surface.

Step S210 is further described with reference to FIG. 4. The control module determines whether $V2-V0>Vq$ is satisfied. Referring to FIG. 4, if the liquid amount is sufficient, after the liquid suction, the sampling probe is still immersed in the liquid surface, and the signal generated at this time is apparently different from the signal generated before the sampling probe contacts the liquid surface, so that $V2-V0>Vq$ is satisfied, indicating that the liquid suction is correct, and the subsequent operations are performed. If the liquid amount is insufficient, the sampling probe departs from the liquid surface during the liquid suction, and recovers to the state before contacting the liquid surface, so that $V2-V0>Vq$ is not satisfied, an alarm is made in the case of insufficient suction, and the current sample adding process is stopped. In FIG. 4, Vq is set to be the same as Vp, but in practical applications, Vq may be different from Vp, which is determined according to actual requirements.

In the above process, two detection and determination steps are performed to respectively determine in the cases of the unreal liquid surface signal generated under the interferences and the insufficient liquid suction. In practical applications, the two detection steps may be performed independently or performed together to determine whether the liquid suction is sufficient.

The sampling probe 400 may be made of a conducting material, and may adopt a reusable probe structure or a disposable tip.

The detection module 100 and the sampling probe 400 can work together to collect and process the signal. One method is to detect the change of the capacitance or inductance before and after the sampling probe 400 contacts the liquid surface, or detect the change of the resistance after the sampling probe 400 contacts the liquid surface.

Figure 5:
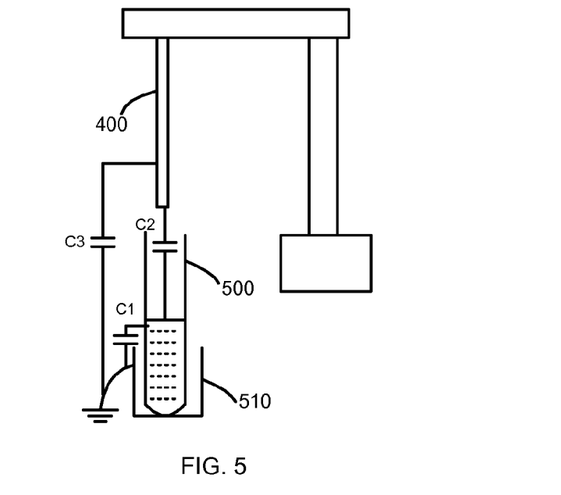
FIG. 5 is a schematic structural view of a sampling device.

The method of detecting the change of the capacitance or the inductance is similar, and the detection of the change of the capacitance is taken as an example for illustration herein. As shown in FIG. 5, before the sampling probe 400 contacts the liquid surface, a capacitance C1 between the liquid to be tested and the ground, a capacitance C2 between the sampling probe 400 and the liquid to be tested, and a capacitance C3 between the sampling probe and the ground exist in the system, so the total capacitance between the sampling probe 400 and the ground is $Cp1=C3+C1*C2/(C1+C2)$. When the sampling probe 400 contacts the liquid surface, C2 approaches infinity, $Cp2=C3+C1$, and the capacitance is increased by $\Delta C=Cp2-Cp1=(C1*C1)/(C1+C2)$.

Figure 6:
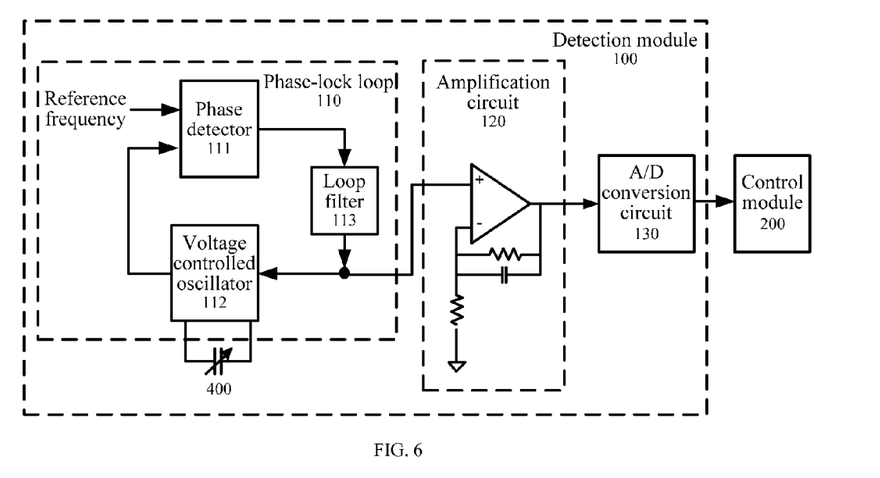
FIG. 6 is a schematic structural view of a part of a circuit.

As shown in FIG. 6, the detection module 100 may include a phase-lock loop 110 for detecting an equivalent capacitance value of the sampling probe 400, and converting the equivalent capacitance value into a corresponding analog voltage signal; an amplification circuit 120 for amplifying the analog voltage signal output by the phase-lock loop 110; and an A/D conversion circuit 130 for converting the analog voltage signal output by the amplification circuit 120 into a corresponding digital signal, and outputting the digital signal to the control module 200.

In one embodiment, the phase-lock loop 110 includes a phase detector 111, a loop filter 113, and a voltage controlled oscillator 112 arranged in a sequentially closed-loop coupled manner. The loop filter 113 outputs the analog voltage signal to the amplification circuit 120; the voltage controlled oscillator 112 is coupled to the sampling probe 400; and the phase detector 110 inputs a reference frequency.

The detection module 100 may detect, amplify, and A/D convert the equivalent capacitance value of the sampling probe 400 through the phase-lock loop 110, and transmit the converted digital signal to the control module 200. The total capacitance between the sampling probe 400 and the ground is introduced to the voltage controlled oscillator 112, an output signal of the voltage controlled oscillator 112 is compared with a reference frequency signal through the phase detector 111, and an output voltage is fed back to the voltage controlled oscillator 112 through the loop filter 113, so as to control the output signal of the voltage controlled oscillator 112, and enable the output signal to have the same frequency as the reference frequency signal, thereby achieving a stable state.

When the sampling probe 400 contacts the liquid surface, the total capacitance between the sampling probe 400 and the ground is increased, the frequency of the output signal of the voltage controlled oscillator 112 is decreased, and the control signal after the comparison of the phase detector 111 and the processing of the loop filter 113 is increased, so that the frequency of the output signal of the voltage controlled oscillator 112 is increased to be the same as the frequency of the reference frequency signal to achieve a stable state.

In this process, the change of the total capacitance between the sampling probe 400 and the ground is converted to the change of the control signal after the processing of the loop filter. The signal is processed by the amplification circuit 120, converted into the digital signal through the A/D conversion circuit 130, and transmitted to the control module 200. The above signal change process may refer to FIG. 4. A skilled artisan will recognize that other methods for implementing detection and conversion of the capacitance and inductance are also applicable, e.g., a bridge method.

Figure 7:
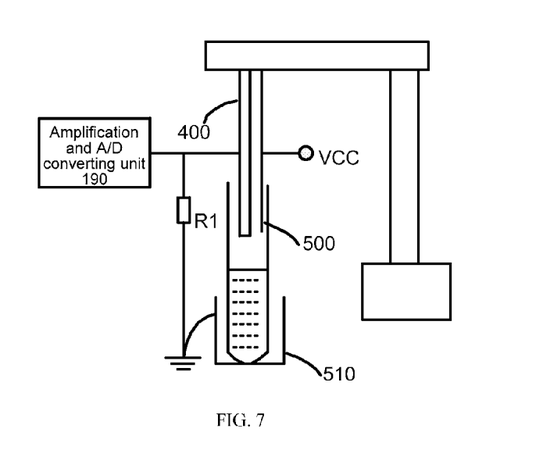
FIGS. 7 and 8 are schematic structural views of a sampling device
Figure 8:
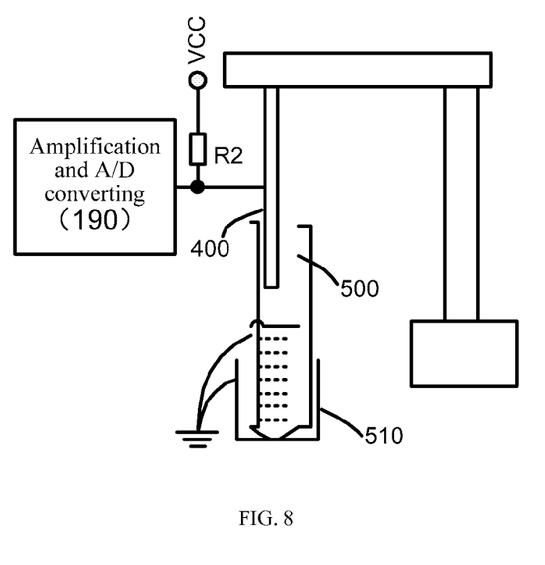

As shown in FIGS. 7 and 8, the detection module 100 may detect a relevant resistance value of the sampling probe 400 based on the principle that, by using the characteristic that the liquid is a conductor, the on/off state of the conductor is different before and after the sampling probe contacts the liquid surface.

In the depicted embodiment, the sampling probe 400 is a double-tube structure, including a first tube and a second tube separated from each other. The detection module 100 includes an amplifier and an A/D converter 190 for amplifying an input analog electric signal and converting the analog electric signal into a corresponding digital signal, and a current-limiting resistor R1.

The first tube is coupled to a high voltage level Vcc, two ends of the current-limiting resistor R1 are respectively coupled to an input end of the amplification and A/D converting unit 190 and ground, and the input end of the amplification and A/D converting unit 190 is further coupled to the second tube and outputs a digital electric signal to the control module 200.

Before the sampling probe contacts the liquid surface, the first tube is insulated from the second tube, and the output signal is pulled down to ground and is at a low level. After the sampling probe contacts the liquid surface, the two tubes are conducted, the output signal is increased to approach a value of Vcc, and the subsequent signal processing is performed.

If the container 500 is a conductor and is grounded, as shown in FIG. 8, the detection module 100 includes an amplifier and A/D converter 190 for amplifying an input analog electric signal and converting the analog electric signal into a corresponding digital signal, and a current-limiting resistor R2.

One end of the current-limiting resistor R2 may be coupled to an input end of the amplifier and A/D converter 190 and the sampling probe 400, and the other end may be coupled to a high voltage level Vcc.

Before the sampling probe 400 contacts the liquid surface, the output voltage is Vcc. After the sampling probe 400 contacts the liquid surface, the probe 400 is grounded because the liquid is grounded and in contact with the probe 400, and therefore the output signal is decreased to a level approaching the ground. In this case, the foregoing signal change diagram and comparison algorithm only need to be correspondingly adjusted to a decreasing mode.

In view of the above, the system is able to detect that a sampling probe appears to contact (but does not contact) the liquid surface due to interferences in the liquid suction process, and detect the situation of insufficient liquid suction, thus avoiding incorrect test results. The system can be widely applied to a sampling system, reagent adding system, and the like.

Although various embodiments have been disclosed above in detail, the invention is not limited to these embodiments. Skilled artisans can make simple changes without departing from the spirit or scope of the invention, and all such changes are deemed to be within the scope of the invention.

What is claimed is:

1. A sampling device, comprising:
   a sampling probe;
   an action module for actuating the sampling probe;
   a control module for controlling the action module;
   a detection module for detecting a change of a relevant physical quantity of the sampling probe and converting the physical quantity into a corresponding electric signal output to the control module,
   wherein the control module processes the electric signal output by the detection module, and controls the action module to actuate the sampling probe based on the electric signal, and determines liquid suction situation based on whether the change of the relevant physical quantity persists over time, the relevant physical quantity of the sampling probe is at least one of a capacitance value of the sampling probe, a resistance value of the sampling probe, and an inductance value of the sampling probe.

2. The sampling device according to claim 1, wherein the change of the relevant physical quantity of the sampling probe is detected as the sampling probe is moved toward a sample surface.

3. The sampling device according to claim 2, wherein the change of the relevant physical quantity is associated with a position of the sampling probe with respect to the sample surface.

4. The sampling device according to claim 1, wherein the sampling probe is made of a conducting material.

5. The sampling device according to claim 4, wherein the detection module comprises:
   a phase-lock loop for detecting an equivalent capacitance value of the sampling probe and converting the equivalent capacitance value into a corresponding analog voltage signal;
   an amplification circuit for amplifying the analog voltage signal output by the phase-lock loop; and
   an analog-to-digital (A/D) conversion circuit, for converting the analog voltage signal output by the amplification circuit into a corresponding digital signal, and outputting the digital signal as the electric signal to the control module.

6. The sampling device according to claim 5, wherein the phase-lock loop comprises a phase detector, a loop filter, and a voltage controlled oscillator arranged in a sequentially closed-loop coupled manner,
   wherein the loop filter outputs the analog voltage signal to the amplification circuit, the voltage controlled oscillator is coupled to the sampling probe and the phase detector receives a reference frequency as an input.

7. The sampling device according to claim 1, wherein the action module comprises a driving unit, a stepper motor, and a rocker arm,
   wherein the driving unit drives the stepper motor to rotate under the control of the control module, the stepper motor propels the rocker arm to move, and the rocker arm propels the sampling probe to move.

8. The sampling device according to claim 1, wherein the electric signal indicates that the sampling probe has contacted an actual sample surface based on the change of the relevant physical quantity persisting over time.

9. The sampling device according to claim 1, wherein the electric signal indicates that the sampling probe has conducted a sample surface bubble.

10. The sampling device accordingly to claim 1, wherein the electric signal indicates that there is an insufficient amount of a sample.

11. The sampling device according to claim 1, wherein the action module actuates the sampling probe to move to an assigned position, the detection module obtains a corresponding electric signal V0, the sampling probe moves downward to reach a target liquid surface; if the detection module detects a sudden change of the relevant physical quantity of the sampling probe within a certain period of time, the sampling probe stops moving and delays for a period of time, the detection module obtains a corresponding electric signal V1, the control module determines whether the sampling probe contacts a liquid surface based on whether a difference between V1 and V0 exceeds a threshold Vp.

12. The sampling device according to claim 11, wherein if the difference between V1 and V0 does not exceed the threshold Vp, the control module determines the sampling probe has experienced interferences.

13. The sampling device according to claim 11, wherein if the difference between V1 and V0 exceeds the threshold Vp, the action module actuates the sampling probe to draw the liquid, after the sampling probe completes the liquid suction, the detection module obtains a corresponding electric signal V2, the control module determines whether a liquid amount is insufficient based on whether a difference between V2 and V0 exceeds a threshold Vq.

14. A sampling device, comprising:
a sampling probe;
an action module for actuating the sampling probe;
a control module for controlling the action module;
a detection module for detecting a change of a relevant physical quantity of the sampling probe and converting the physical quantity into a corresponding electric signal output to the control module,
wherein the control module processes the electric signal output by the detection module, and controls the action module to actuate the sampling probe based on the electric signal, wherein the sampling probe comprises a first tube and a second tube separated from each other,
the detection module comprises an amplifier and A/D converter, for amplifying an input analog signal and converting the analog signal into a corresponding digital signal output as the electric signal, and a current-limiting resistor; and
the first tube is coupled to a high voltage level, two ends of the current-limiting resistor are respectively coupled to an input end of the amplifier and A/D converter and ground, and the input end of the amplifier and A/D converter is further coupled to the second tube and outputs the digital signal as the electric signal provided to the control module.

15. A sampling device, comprising:
a sampling probe;
an action module for actuating the sampling probe;
a control module for controlling the action module;
a detection module for detecting a change of a relevant physical quantity of the sampling probe and converting the physical quantity into a corresponding electric signal output to the control module,
wherein the control module processes the electric signal output by the detection module, and controls the action module to actuate the sampling probe based on the electric signal, wherein a container for containing a target liquid is comprises a conductive material and is grounded;
the detection module comprises an amplifier and A/D converter, for amplifying an input analog electric signal and converting the analog electric signal into a corresponding digital signal output as the electric signal provided to the control module, and a current-limiting resistor; and
one end of the current-limiting resistor is coupled to an input end of the amplifier and A/D converter and the sampling probe, and the other end is coupled to a high voltage level.

* * * * *